United States Patent
Kindred et al.

(10) Patent No.: US 8,254,829 B1
(45) Date of Patent: Aug. 28, 2012

(54) NETWORK MEDIA SERVICE WITH TRACK DELIVERY ADAPTED TO A USER CADENCE

(75) Inventors: Jonathan R. Kindred, Olathe, KS (US); Geoffrey S. Martin, Overland Park, KS (US); Danny L. Bowman, Overland Park, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 1146 days.

(21) Appl. No.: 12/118,034

(22) Filed: May 9, 2008

(51) Int. Cl.
*H04W 4/02* (2009.01)

(52) U.S. Cl. ............................... 455/3.06; 455/414.1

(58) Field of Classification Search .................. None
See application file for complete search history.

(56) References Cited

U.S. PATENT DOCUMENTS

| | | | |
|---|---|---|---|
| 7,089,020 B2 | 8/2006 | Asthana et al. | |
| 7,737,353 B2 * | 6/2010 | Sasaki et al. | 84/612 |
| 2007/0074618 A1 * | 4/2007 | Vergo | 84/612 |
| 2007/0089057 A1 | 4/2007 | Kindig | |
| 2008/0126384 A1 * | 5/2008 | Toms et al. | 707/102 |
| 2011/0179943 A1 * | 7/2011 | Bowen | 84/612 |

OTHER PUBLICATIONS

Groove Mobile, Music Solution Overview, Brochure, Nov. 2008.

\* cited by examiner

*Primary Examiner* — Philip Sobutka

(57) ABSTRACT

A wireless network service delivers audio tracks to a user via a mobile wireless terminal. A server maintains a plurality of audio tracks, wherein each audio track is stored in conjunction with a respective cadence tag. A cadence evaluator identifies a substantially instantaneous user status and selects a cadence tag corresponding to the user status. The server streams a selected audio track having a cadence tag matching the selected cadence tag, and the mobile wireless terminal plays it back to the user. The cadence can be selected to match a desired pace of an athletic workout, a desired heart rate, or the particular geographic surroundings, for example.

30 Claims, 3 Drawing Sheets

| Zone | Cadence |
|------|---------|
| Z1 | C1 |
| Z2 | C2 |
| Z3 | C3 |
| Z4 | C1 |
| Z5 | C4 |

| Speed | Cadence |
|-------|---------|
| S1 | C1 |
| S2 | C2 |
| S3 | C3 |
| S4 | C4 |
| S5 | C5 |

|    | S1 | S2 | S3 | S4 | S5 |
|----|----|----|----|----|----|
| Z1 | C1 | C2 | C3 | C3 | C4 |
| Z2 | C3 | C3 | C4 | C4 | C5 |
| Z3 | C1 | C2 | C2 | C3 | C3 |
| Z4 | C2 | C2 | C3 | C2 | C2 |
| Z5 | C1 | C1 | C3 | C3 | C4 |

NETWORK MEDIA SERVICE WITH TRACK DELIVERY ADAPTED TO A USER CADENCE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to wireless distribution of audio tracks, and, more specifically, to automatic playback of audio tracks according to a cadence associated with the activity or surroundings of the user.

Wireless communication service providers, such as cellular or PCS providers, have introduced many new desirable services and the capabilities of the network infrastructure and the user terminals have advanced. For example, cellular handsets are now available having audio storage, processing, and reproduction capabilities similar to many standalone personal music players, such as mp3 players. The user carries only one device to serve as a cellular phone and music player.

To help the user take advantage of the audio player capabilities of their cellular phone, cellular service providers have introduced music distribution services through which the user can download audio tracks to their phone/player. In addition to purchasing song downloads individually, subscription services are being offered that allow unlimited downloads and/or live streaming of audio tracks from playlists or quasi-radio stations. As data transport capacity and speed have increased, it has also become feasible to stream purchased or subscription tracks over the network each time is it listened to instead of storing it in the user terminal.

Users of music players and music services frequently create playlists of tracks that are associated with particular situations or events so that only tracks selected to be in the playlist are heard when the user activates the playlist. For example, many people enjoy listening to music during athletic workouts, such as jogging and bicycling. A playlist to be used during a particular type of workout can include audio tracks chosen for their pace (e.g., tempo measured in beats per minute). For example, a playlist to be used while traversing a bicycling route can include tracks with a fast tempo. Alternatively, a playlist may correspond to a landmark or location (e.g., slow, peaceful audio tracks on a playlist to be used while hiking a nature trail). The occasions for which a playlist is defined and the tracks meeting the criteria for inclusion on the playlist can be arbitrarily defined by the user, or they may include stock playlists defined by the service provider using ordinary criteria.

Manually selecting playlists often becomes inconvenient during quickly changing situations or where the user is too preoccupied to easily make a new selection. Continuing with the bicycling example, the user may cycle over a route that passes through different upward and downward slopes along with level sections. They may be expending a high level of effort while moving relatively slowly (e.g., traversing up a steep slope) or moving quickly with low effort (e.g., gliding down a hill), with the appropriate playlist for each part of the route having songs of a corresponding tempo. Also during the route, they may pass by a particular landmark and want to listen to another playlist that was not set up based on the tempo. However, it can be undesirable to attempt to change playlists to follow the changing situation while engaged in an activity.

SUMMARY OF THE INVENTION

The present invention has the advantage of automatically reproducing audio tracks having a cadence that matches the user's status. As used herein, cadence refers to a perceived characteristic of an audio track matching pre-defined situations in terms of tempo, pace, landmarks, or surrounding, for example.

In one aspect of the present invention, a wireless network service delivers audio tracks to a user via a mobile wireless terminal. A server maintains a plurality of audio tracks, wherein each audio track is stored in conjunction with a respective cadence tag. A cadence evaluator identifies a substantially instantaneous user status and selects a cadence tag corresponding to the user status. The server delivers and the mobile wireless terminal reproduces a selected audio track having a cadence tag matching the selected cadence tag.

DETAILED DESCRIPTION OF PREFERRED EMBODIMENTS

In one preferred embodiment, this invention tracks a user's running or cycling cadence along with their location and matches both parameters against a database of established playlists which may be created by the user, by a user community, or by the network service provider. The invention then streams the selected music to the user that corresponds to their terrain and pace.

Most distance athletes train locally along well known routes, and they tend to have regular speeds and/or effort levels along their typical routes. The average speed of cyclists along a route with a combination of hilly and flat terrain tends to fall into four groupings that are substantially stable over time, specifically 1) high exertion with high speed, 2) high exertion with medium speed, 3) low exertion with high speed, and 4) low exertion with low speed. Nevertheless, the cyclist may also sometimes attack a route differently so that certain parts of the route may be traversed with an atypical exertion level. The present invention can be set up to take into account only the particular location in which the user is present or may alternatively be set up to select an audio track based on both the location and the speed, only the speed, or any combination of these and other factors.

The cadence (e.g., tempo, pace, theme, or ambiance) of a track can also be used to encourage a change in the level of exertion expended by the user. Many runners participate in jogging due to heart health benefits. To achieve these, it is important to maintain a target heart rate during a run. By linking a heart rate monitor to the wireless terminal, the present invention selects an audio track having either a faster or slower tempo when the runner's measured heart rate is below or above the target heart rate, respectively, in order to encourage a corresponding change in the running pace.

The invention can be structured as a music distribution service that determines an athlete's location (e.g., by periodically sending signal pings from the mobile terminal to the nearest base stations to triangulate a position, or by using a GPS receiver). Based on the basic location information, program logic on the athlete's mobile terminal determines their cadence and transmits it to the service. Users create playlists for various route segments in advance using a web-based tool. The user's playlists are stored as directory files that reference stored media content (e.g., audio tracks) on a web server. When creating playlists, metadata in the form of cadence tags that correspond to common speeds and effort levels are provided to identify the playlists. In response to the instantaneous cadence, a playlist is selected with metadata that best corresponds to the location and activity of the user. The service then streams media from the selected playlist to the user (or activates tracks previously downloaded to the mobile terminal).

Figure 1:
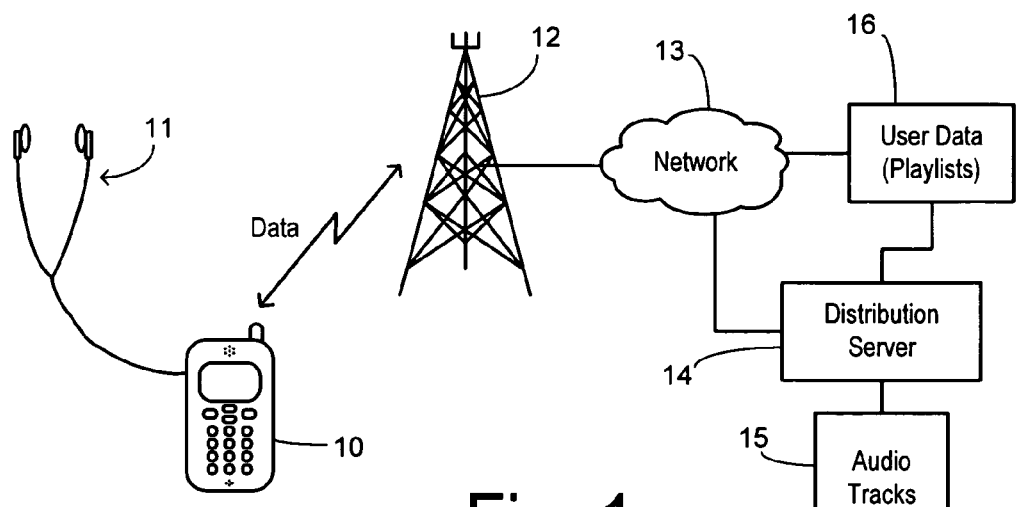
FIG. 1 is a network diagram showing a prior art music distribution service.

Referring now to FIG. 1, a conventional wireless telecommunications network is shown for providing a music distribution service. A mobile wireless terminal 10, such as a cellular telephone handset, has an internal audio player for connecting to a headphone speaker set 11. Audio tracks are obtained using a data connection through a base transceiver station (BTS) 12 to a home network 13. A distribution server 14 either resides within network 13 or is remotely connected to it through a gateway and/or intervening networks, such as the Internet (not shown). A database of audio tracks 15 is connected to server 14 so that track selections made by an authorized user can be transmitted (e.g., streamed) to terminal 10. A database 16 of user data is coupled to network 13 and distribution server 15 to facilitate user authentication and to handle storage of user specific information, such as private playlists. Such a conventional system, however, lacks any ability to determine a user's cadence (e.g., their location, speed, heart rate, surroundings, or proximity to landmarks) or to dynamically change playlists in response to changes in cadence.

Figure 2:
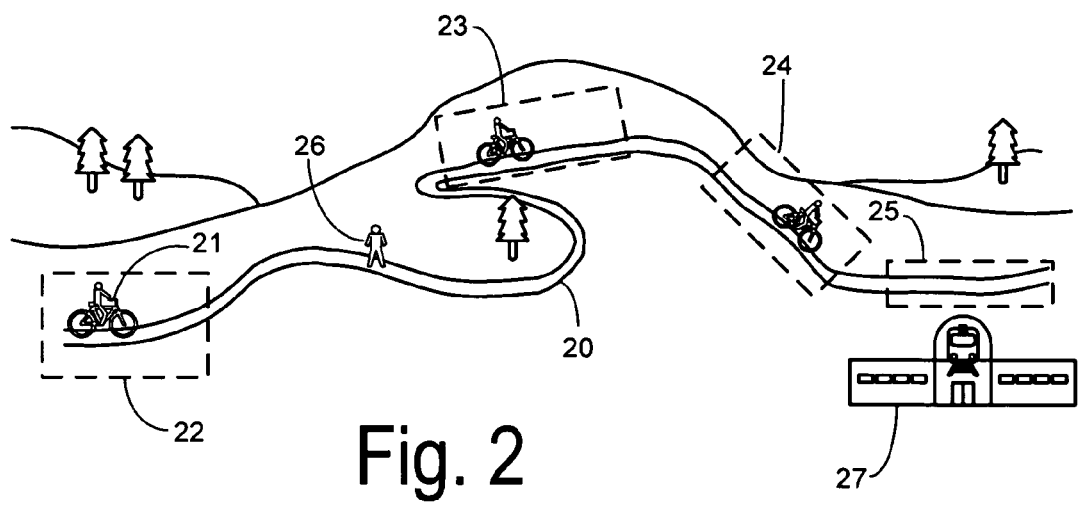
FIG. 2 shows a cycling/walking/jogging route passing through different types of terrain for which different types of audio tracks could be desirable.

FIG. 2 shows an athletic training route 20 that passes through various hilly and flat terrain. A cyclist 21 is traversing route 20 while using the music distribution service. A plurality of predetermined zones 22-25 are defined according to specific geographic locations based on respective ranges of geographic coordinates. Either the user, a community of users, or the service provider identify desired zones wherein each zone exhibits one specific type of terrain. For example, zones 22 and 23 represent respective uphill slopes, zone 24 represents a steep downhill slope, and zone 25 represents level terrain. By monitoring both the zone and the speed (based on changing location) within the zone, the present invention can refine the identified cadence so that it matches a level or exertion and may also determine direction of travel and a type of conveyance. Thus, a runner 26 is also present on route 20. Based on the speed of movement or based on a manual setting made by the user, a type of conveyance such as cycling or on foot can be determined and used in selecting a cadence tag to be associated with the user's instantaneous user status (e.g., where they are, how fast they are moving, their mode of conveyance, and their actual and target heart rates).

In an alternative embodiment wherein the cadence is based on proximity to a predetermined landmark, zone 25 is shown as being adjacent to a landmark 27 such as a train station. A cadence tag associated with landmark 27 could be used to identify a playlist of audio tracks for songs about trains and railroads, for example. Another landmark-based cadence tag could be associated with a particular rural or urban setting, allowing playlists to be defined for those settings.

Figures 3, 4, 5, 6:
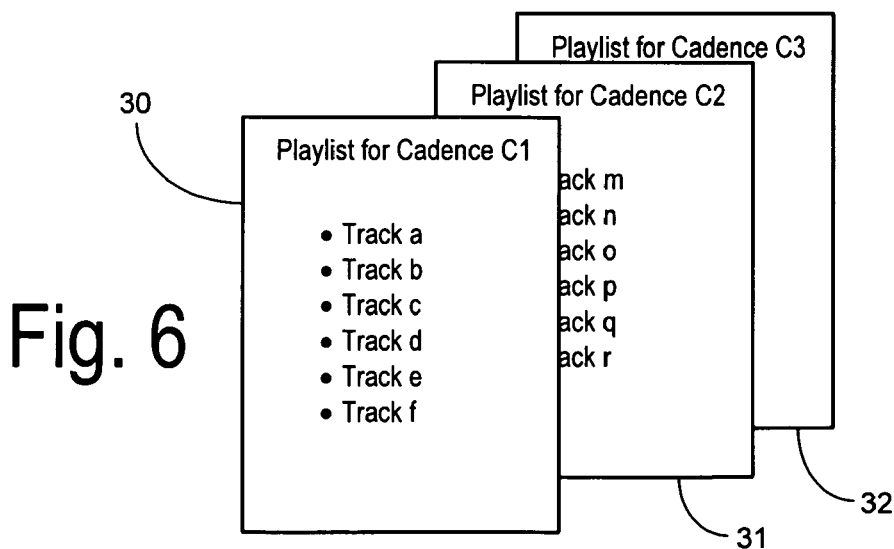
FIG. 3 is a table showing a mapping from a particular geographic zone to a corresponding cadence tag.
FIG. 4 is a table showing a mapping from a particular speed of travel to a corresponding cadence tag.
FIG. 5 is a multi-dimensional table showing a mapping from a particular geographic zones and speed of travel to corresponding cadence tags.
FIG. 6 illustrates a plurality of playlists that can be customized for individual users or can be published for use by a group of users.

The cadence calculated for a user at any particular time is based on their substantially instantaneous user status. In various preferred embodiments of the invention, the user status is based on 1) presence in a particular zone, 2) the speed at which the user is moving, 3) both the zone and the speed, 4) the target heart rate of the user, and 5) the difference between the target heart rate and the actual heart rate. In response to the user status, a lookup table or map can be used to identify a cadence tag that serves as a link to the playlist(s) or audio tracks with a matching cadence. FIG. 3 shows a mapping between zones Z1 to Z5 and the predetermined cadence tags C1 to C4 that have been selected by the user or the user community. Similarly, FIG. 4 shows a mapping from various speed ranges S1 to S5 to corresponding cadence tags C1 to C5. In one simple embodiment, each cadence tag may correspond to a respective range in tempo as measured in beats per minute (BPM). For example, cadence C1 includes music tracks with a BPM from 40 to 70 while cadence C2 includes music tracks with a BPM from 71 to 100.

The mapping from the user's instantaneous status to the cadence can also be multi-dimensional. As shown in FIG. 5, a two-dimensional lookup table correlates a combination of each predetermined zone with respective speed ranges to identify a cadence tag that better reflects the exertion expended by the user since both the terrain and the speed are known. A third dimension may be added to the table based on the type of conveyance being used (i.e., a slower speed when running would indicate a greater exertion than when cycling at the same speed).

Based on the cadence values of interest as defined by the user, the user community, or the service provider, at least one playlist is created corresponding to each cadence tag as shown in FIG. 6. Thus, a playlist 30 is identified with cadence tag C1 and includes a plurality of audio tracks a-f. Playlists 31 and 32 are created for cadence tags C2 and C3, respectively. When accessed, the tracks identified by a particular playlist can be played randomly or in any specified order.

Figure 7:
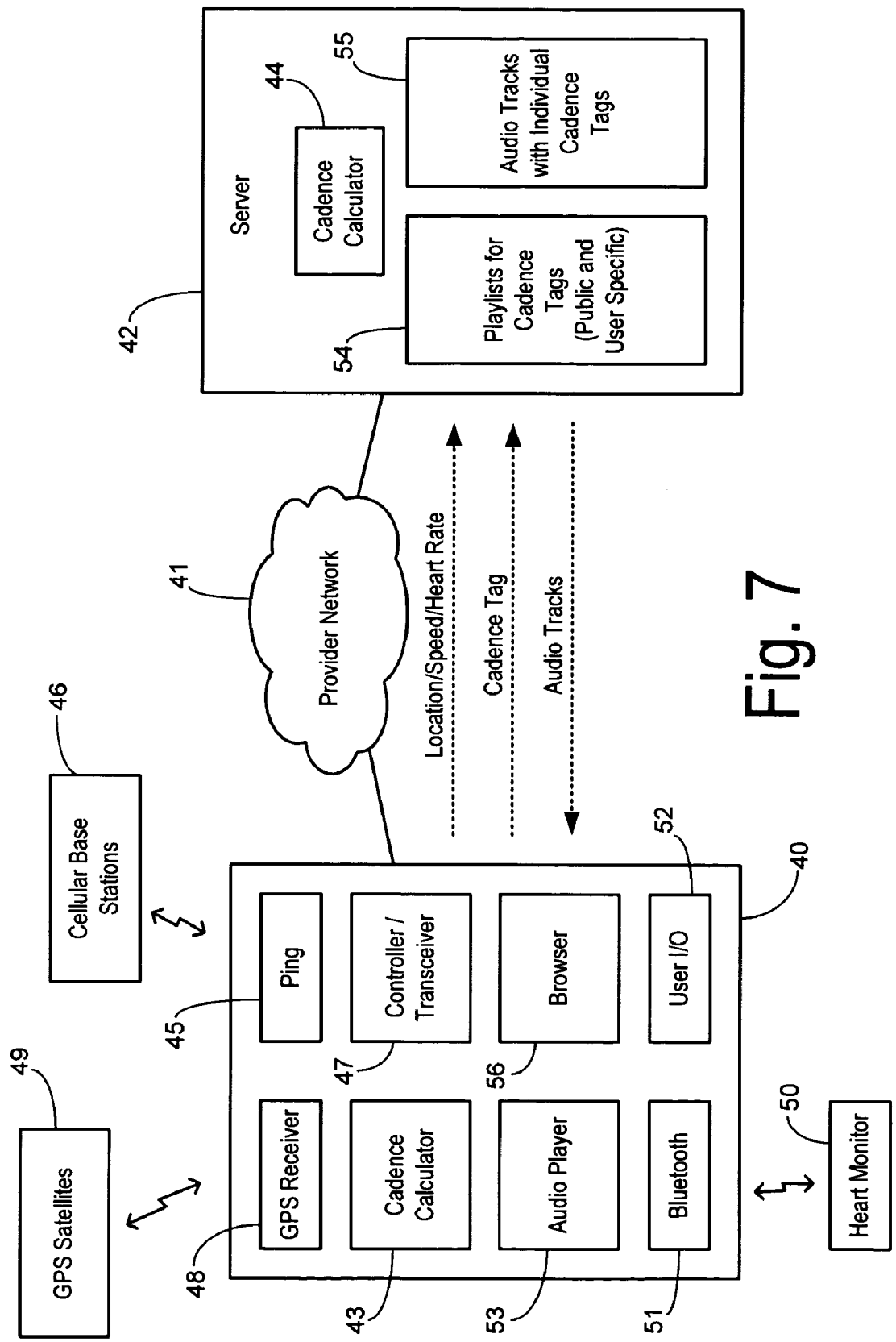
FIG. 7 is a block diagram showing the invention in greater detail.

The wireless network service of the present invention is shown in greater detail in FIG. 7. Mobile wireless terminal 40 has a data connection to provider network 41 through which it accesses a distribution server 42. A cadence calculator 43 in terminal 40 and/or a cadence calculator 44 in server 42 identifies a substantially instantaneous user status and selects a cadence tag corresponding to the user status. The user status is determined in response to the geographic location of mobile terminal 40 and on other variables. The mapping of the location and other variables to a cadence can be performed directly by cadence calculator 43, in which case cadence calculator 44 in server 42 is unnecessary. When cadence calculator 44 is used, sensed data and/or user entered variables (e.g., location, speed, and heart rate) are transmitted from terminal 40 to server 42 in order to support the identification of the user status.

To determine an instantaneous geographic location of terminal 40, a ping block 45 is provided for sending periodic pings to several nearby cellular base stations 46. Based on the known locations of base stations 46 and analysis of the ping signals to identify the distance to each base station 46, the location of terminal 40 is determined by triangulation as is known in the art (e.g., U.S. Pat. No. 7,089,020 issued to Asthana et al). Alternatively, a GPS receiver 48 may be provided in terminal 40 to determine the instantaneous geographic position in response to positioning signals from GPS satellites 49.

To determine heart rate as a factor in the instantaneous user status, a heart monitor 50 is strapped to the wrist or chest of the user to measure heart rate in a conventional manner. Monitor 50 preferably includes a wireless transceiver, such as a Bluetooth node, for transmitting the heart rate data to a Bluetooth transceiver 51 in terminal 51. A target heart rate is supplied to cadence calculator 43 manually via a user I/O interface 52 such as a keypad or touchscreen. I/O interface 52 can also be used to provide a type of conveyance being used during the athletic workout.

Once the cadence tag corresponding to the instantaneous user status has been identified by cadence calculator 43 or 44, a matching audio track is identified for playing back to the user. The matching playlists and/or tracks may have been previously downloaded to terminal 40 so that an audio player 53 can begin the playback or request a specific track. Preferably, server 42 streams selected tracks over network 41 to audio player 53 in real time. Server 42 selects an audio track for delivery to terminal 40 based on the identified cadence tag and either the playlists in playlist database 54 or direct access to tagged audio tracks in track database 55. Thus, in a manner similar to standard tags contained in mp3 audio files, each audio track has an appended cadence tag. If cadence tags are applied to each individual track in database 55, then creation of playlists for database 54 can be greatly simplified, since a user could search for audio tracks having a tempo in a particular range of BPMs.

In order to support creation of playlists, server 42 is preferably accessible to authorized users for customizing playlists in database 54. A browser 56 is provided in terminal 40 for signing on to database 54 and performing customizing operations. Alternatively, server 42 may also be accessible to the user via the Internet in order to customize playlists and cadence tags in advance. Cadence calculators 43 and 44 may also be user configurable to define zones or speed ranges used in identifying various cadence tags, for example.

What is claimed is:

1. A wireless network service for delivering audio tracks to a user via a mobile wireless terminal, comprising;
    a server for maintaining a plurality of audio tracks, wherein each audio track is stored in conjunction with a respective cadence tag; and
    a cadence evaluator that identifies a substantially instantaneous user status and selects a cadence tag corresponding to the user status, wherein the substantially instantaneous user status comprises a geographic location within a plurality of predetermined zones, and wherein the cadence evaluator includes a mapping for associating each zone with at least one respective cadence tag;
    wherein the server delivers and the mobile wireless terminal reproduces a selected audio track having a cadence tag matching the selected cadence tag.

2. The network service of claim 1 wherein the respective cadence tag for each audio track is predetermined based on a musical tempo in beats per minute.

3. The network service of claim 1 wherein the mobile wireless terminal is comprised of a cellular telephone adapted to determine the geographic location in response to triangulation between a plurality of cellular base transceiver stations.

4. The network service of claim 1 wherein the mobile wireless terminal is comprised of a cellular telephone adapted to determine the geographic location in response to GPS signals.

5. The network service of claim 1 wherein the substantially instantaneous user status comprises a speed of movement of the mobile wireless terminal, and wherein the cadence evaluator includes a mapping for associating respective speeds with at least one respective cadence tag.

6. The network service of claim 5 wherein the mobile wireless terminal is comprised of a cellular telephone adapted to determine the speed in response to triangulation between a plurality of cellular base transceiver stations.

7. The network service of claim 5 wherein the mobile wireless terminal is comprised of a cellular telephone adapted to determine the speed in response to GPS signals.

8. The network service of claim 1 wherein the substantially instantaneous user status comprises a speed of movement of the mobile wireless terminal and a type of conveyance, and wherein the cadence evaluator includes a mapping for associating respective speeds and types of conveyance with at least one respective cadence tag.

9. The network service of claim 8 wherein the types of conveyance include cycling and on foot.

10. The network service of claim 1 wherein the substantially instantaneous user status comprises a measured heart rate of the user, and wherein the cadence evaluator includes a mapping for associating the measured heart rate with at least one respective cadence tag.

11. The network service of claim 10 wherein the mobile wireless terminal is adapted to interface with a heart monitor worn by the user to obtain the measured heart rate.

12. The network service of claim 1 wherein the substantially instantaneous user status comprises a measured heart rate of the user and a target heart rate, and wherein the cadence evaluator includes a mapping for associating the measured heart rate and target heart rate with at least one respective cadence tag.

13. The network service of claim 1 wherein the cadence evaluator is in the mobile wireless terminal, and wherein the selected cadence tag is wirelessly transmitted to the server.

14. The network service of claim 1 wherein the server maintains a plurality of playlists, wherein each playlist identifies a plurality of the audio tracks having the same respective cadence tag, wherein the server selects a particular playlist in response to the selected cadence tag, and wherein the server streams an audio track included in the selected playlist to the mobile wireless terminal.

15. The network service of claim 14 wherein the server is accessible to the user to customize the playlists in advance.

16. The network service of claim 1 wherein the server is accessible to the user to customize the respective cadence tags associated with the audio tracks in advance.

17. A network service for delivering audio tracks to a user via a mobile wireless terminal, comprising;
    a server for maintaining a plurality of audio tracks, wherein each audio track is stored in conjunction with a respective cadence tag; and
    a cadence evaluator that identifies a substantially instantaneous user status and selects a cadence tag corresponding to the user status;
    wherein the server delivers and the mobile wireless terminal reproduces a selected audio track having a cadence tag matching the selected cadence tag; and
    wherein the respective cadence tag for each audio track is predetermined based on at least one predetermined geographic landmark.

18. A method of delivering audio tracks to a user's mobile wireless terminal over a wireless network, comprising the steps of:
- maintaining a plurality of audio tracks for delivery to the mobile wireless terminal via the wireless network,
- pre-defining a respective cadence tag for each audio track to be stored in conjunction therewith;
- identifying a substantially instantaneous user status by calculating a geographic location of the mobile wireless terminal within a plurality of predetermined zones;
- selecting a cadence tag corresponding to the user status by looking up at least one respective cadence tag in a mapping in response to the calculated zone; and
- reproducing a selected audio track on the mobile wireless terminal having a cadence tag matching the selected cadence tag.

19. The method of claim 18 wherein the respective cadence tag for each audio track is predetermined based on a musical tempo in beats per minute.

20. The method of claim 18 wherein the mobile wireless terminal is comprised of a cellular telephone, and wherein the step of calculating the geographic location comprises a triangulation between a plurality of cellular base transceiver stations.

21. The method of claim 18 wherein the mobile wireless terminal is comprised of a cellular telephone, and wherein the step of calculating the geographic location uses GPS signals.

22. The method of claim 18 wherein the step of identifying a substantially instantaneous user status comprises calculating a speed of movement of the mobile wireless terminal, and wherein the step of selecting a cadence tag comprises looking up at least one respective cadence tag in a mapping in response to the calculated speed.

23. The method of claim 18 wherein the step of identifying a substantially instantaneous user status comprises calculating a speed of movement of the mobile wireless terminal and detecting a type of conveyance, and wherein the step of selecting a cadence tag comprises looking up at least one respective cadence tag in a mapping in response to the speed and the type of conveyance.

24. The method of claim 23 wherein the types of conveyance include cycling and on foot.

25. The method of claim 18 wherein the step of identifying a substantially instantaneous user status comprises measuring a heart rate of the user, and wherein the step of selecting a cadence tag comprises looking up at least one respective cadence tag in a mapping in response to the measured heart rate.

26. The method of claim 18 wherein the step of identifying a substantially instantaneous user status comprises measuring a heart rate of the user and determining a target heart rate, and wherein the step of selecting a cadence tag comprises looking up at least one respective cadence tag in a mapping in response to the measured heart rate and the target heart rate.

27. The method of claim 18 further comprising the steps of:
- maintaining a plurality of playlists, wherein each playlist identifies a plurality of the audio tracks having the same respective cadence tag;
- selecting the audio track for reproduction from a particular playlist matching the selected cadence tag; and
- streaming the selected audio track to the mobile wireless terminal in real time.

28. The method of claim 27 wherein the server is accessible to the user to customize the playlists in advance.

29. The method of claim 18 wherein cadence tags for the plurality of audio tracks are customized by the user in advance.

30. The method of claim 18 wherein the respective cadence tag for each audio track is predetermined based on at least one predetermined geographic landmark.

* * * * *